United States Patent
Larsson et al.

(10) Patent No.: US 6,537,550 B1
(45) Date of Patent: *Mar. 25, 2003

(54) USE OF AVIAN ANTIBODIES

(75) Inventors: Anders Larsson, Västra Ågatan (SE); Hans Kollberg, Skolgatan (SE)

(73) Assignee: Immun System I.M.S. AB, Uppsala (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,361

(22) PCT Filed: Mar. 20, 1998

(86) PCT No.: PCT/SE98/00526

§ 371 (c)(1),
(2), (4) Date: Sep. 20, 1999

(87) PCT Pub. No.: WO98/41235

PCT Pub. Date: Sep. 24, 1998

(30) Foreign Application Priority Data

Mar. 20, 1997 (SE) ................................................ 9701026

(51) Int. Cl.[7] ...................... A61K 39/395; A61K 39/40; A61K 39/00; A61K 47/00; C12N 1/20

(52) U.S. Cl. ................................ 424/150.1; 424/130.1; 424/137.1; 424/170.1; 424/157.1; 424/134.1; 424/164.1; 435/253.3; 514/851; 530/389.5; 530/387.1; 530/389.1; 530/423; 530/388.2; 530/388.4; 426/47; 426/55; 426/37

(58) Field of Search ............................ 424/170.1, 150.1, 424/157.1, 803, 130.1, 134.1, 164.1, 439, 442, 45, 47; 530/389.5, 387.1, 388.2, 388.4, 389.1, 827, 853, 855, 423; 514/851, 570; 426/47, 55, 32; 435/253.3

(56) References Cited

U.S. PATENT DOCUMENTS

| | | | |
|---|---|---|---|
| 4,714,612 A | * 12/1987 | Nakamura et al. | 424/85 |
| 4,994,269 A | * 2/1991 | Collins et al. | 424/85.8 |
| 5,215,746 A | 6/1993 | Stolle et al. | 424/92 |
| 5,240,704 A | * 8/1993 | Tsurumizu et al. | 424/85.8 |
| 5,290,540 A | * 3/1994 | Prince et al. | 424/45 |
| 5,420,253 A | * 5/1995 | Emery et al. | 530/423 |
| 5,505,945 A | * 4/1996 | Gristina et al. | 424/164.1 |
| 5,530,102 A | * 6/1996 | Gristina et al. | 530/391.1 |
| 5,601,823 A | * 2/1997 | Williams | 424/167.1 |
| 5,681,565 A | * 10/1997 | Gristina et al. | 424/164.1 |
| 5,707,627 A | * 1/1998 | Gristina et al. | 424/64.1 |
| 5,718,899 A | * 2/1998 | Gristina et al. | 424/164.1 |
| 5,759,544 A | * 6/1998 | Harada et al. | 424/137.1 |
| 5,817,312 A | * 10/1998 | Gristina et al. | 424/164.1 |
| 5,922,344 A | * 7/1999 | Hilty et al. | 424/439 |

FOREIGN PATENT DOCUMENTS

| | | | | |
|---|---|---|---|---|
| EP | 0 225 254 | | 6/1987 | |
| EP | 0 503 293 | | 9/1992 | |
| JP | 360028937 A | * | 2/1985 | |
| JP | 01226828 A | * | 3/1988 | ............ A61K/7/16 |
| JP | 406009356 A | * | 1/1994 | |
| JP | 9-20684 | | 1/1997 | |
| JP | 9020684 A | * | 1/1997 | |
| JP | 409002926 A | * | 1/1997 | |
| JP | 409052822 A | * | 2/1997 | |
| WO | 94 13264 | | 6/1994 | |
| WO | WO94/13264 | * | 6/1994 | ............ A61K/9/08 |
| WO | WO 9631186 | * | 10/1996 | |

OTHER PUBLICATIONS

Zrein et al. Arch. Virol. 90: 197–206, 1986.*
Ma et al. Arch. Oral. Biol. 35: Suppl. 115S–122S, 1990.*
Sugita–Konishi et al. Biosci. Biotech. Biochem. 60(5): 886–888, 1996.*
Yokoyama et al. Infect. Immun. 60: 998–1007, abstract, 1992.*
Larsson et al., "Chicken Anti–Protein G for the Detection of Small Amounts of Protein G", *Hybridoma*, vol. 12, No. 1, pp. 143–147, (1993).
Larsson et al., "Chicken Antibodies: A Tool to Avoid Interference by Human Anti–Mouse in ELISA After In vivo Treatment With Murine Monoclonal Antibodies", *Hybridoma*, vol. 11, No. 1, pp. 33–39, (1992).
Hiraga et al., "Prevention of Human Rotavirus Infection with Chicken Egg Yolk Immunoglobulins Containing Rotavirus Antibody in Cat", *Chiken Egg Yolk Immunoglobulins to Rotavirus*, pp. 118–123. No year of publication.
Larsson et al., "Chicken antibodies: a tool to avoid interference immunological assays", *Avian Immunology in Progress*, pp. 97–102, (1993).
Bartz et al., "Prevention of Murine Rotavirus Infection with Chicken Egg Yolk Immunoglobulins", *The Journal Of Infectious Diseases*, vol. 142, No. 3, pp. 439–441, (1980).
Larsson et al., "Chicken antibodies: a tool to avoid false positive results by rheumatoid factor in latex fixation tests", *Journal of Immunological Methods*, vol. 108, pp. 205–208, (1988).
Larsson et al., "Chicken antibodies: a tool to avoid interference by complement activation in ELISA", *Journal of Immunological Methods*, vol. 156, pp. 79–83, (1992).
Larsson et al., "Chicken Antibodies: Taking Advantage of Evolution–A Review", *Reviews*, pp. 1807–1812, (1993).

(List continued on next page.)

Primary Examiner—Nita Minnifield
Assistant Examiner—Khatol Shahnan-Shah
(74) Attorney, Agent, or Firm—Browdy and Neimark, P.L.L.C.

(57) ABSTRACT

The present invention relates to use of avian antibodies and/or antigen binding fragments thereof, for the production of a drug for treatment and/or prevention of respiratory tract infection. The drug is administered through local application at the oral cavity and/or pharynx.

6 Claims, No Drawings

OTHER PUBLICATIONS

Ikemori, et al., "Protection of neonatal calves against fatal enteric colibacillosis by administration of egg yolk powder from hens immunized with K99–piliated enterotoxigenic *Escherichia coli*", *J. Vet Res.,* vol. 53, No. 11, (1992).

Valerius et al., "Prevention of chronic *Pseudomanas aeruginose*, colonization in cystic fibrosis by early treatment", *The Lancet*, vol. 338, pp. 725–726, (1991).

Szaff et al, Frequent Antibiotic Therapy Improves Survival Of Cystic Fibrosis Patients With Chronic *Pseudomonas Aeruginosa, Acta Paediatr Scand*, vol. 72, pp. 651–657, (1983).

Akita et al., "Comparison of four purification methods for the production of immunoglobulins from eggs laid by hens immunized with an enterotoxigenic *E. Coli* strains", *Journal of Immunological Methods*, vol. 60, pp. 207–214, (1993).

Lindahl et al., "Studies of Fibrinogen Binding to Platelets by Flow Cytometry: An Improved Method for Studies of Platelet Activation", *Thrombosis and Haemostasis*, vol. 68, No. 2, pp. 1–5, (1992).

Hoiby et al., "Pseudomonas Infection in Cystic Fibrosis", *Cystic Fibrosis*, vol. 1, pp. 251–268, (1993).

\* cited by examiner

USE OF AVIAN ANTIBODIES

The present application is the national stage under 35 U.S.C. 371 of PCT/SE98/00526, filed Mar. 20, 1998, which claims priority from Swedish application 9701026-8, filed Mar. 20, 1997.

TECHNICAL FIELD

The present invention relates to the use of avian antibodies against infectious antigen for treatment and/or prevention of respiratory tract infections, The antibodies are administered through local application at the oral cavity, and/or pharynx,

BACKGROUND OF THE INVENTION AND PRIOR ART

It is well known that domestic avian species, e.g. hens, produce high titres of antibodies in their eggs against factors against which they have been immunised (4), In several trials avian antibodies have been used to prevent or treat bacterial or viral infections in the digestive tract of different animals with promising results (12–17), but there is no evidence in the scientific literature that avian antibodies, or antibodies of any other origin, have been used in preventing or treating respiratory tract infections, neither in mammals nor humans. Traditionally respiratory tract infections are treated with conventional therapy, such as antibiotic treatment. The reason for not using antibodies is that no possible way of administering the antibodies, when treating respiratory tract infections, has been seen. Most surprisingly, the present inventors found that the administration of antibodies through local application at the oral cavity and/or pharynx could be used to treat respiratory tract infections.

SUMMARY OF THE INVENTION

The present invention suggests, for the first time, use of avian antibodies and/or antigen binding fragments thereof, for the production of a drug for preventing and/or treating respiratory tract infections.

Most surprisingly, the present invention suggests, for the first time, that avian antibodies can be used to prevent and/or treat respiratory tract infections when administered through local application at the oral cavity and/or pharynx, preferably by gargling and/or swallowing. The present inventors have verified this by clinical studies on humans.

The present invention relates to treatment of respiratory tract infections—i.e. infections in the nasal cavity, paranasal sinuses the lymphatic ring in the oropharynx, larinx, trachea, bronchi, bronchioli and/or alveoli, i.e. all the way down the respiratory tree—caused by e.g. Pseudomonads and/or related microorganisms.

Treatment and/or prevention of respiratory tract infections according to the invention are particularly appropriate for those individuals having increased susceptibility to infections or increased risk of catching infections, since the treatment is mild and not accompanied by undesirable side effects.

DETAILED DESCRIPTION OF THE INVENTION

To test the use of antibodies for treating respiratory tract infections the present inventors choose the group of patients suffering from cystic fibrosis (CF). These patients have increased susceptibility to infections with reoccurring or chronic respiratory tract infections of *Pseudomonas aeruginosa*. Cystic fibrosis patients have hitherto had to rely on conventional therapy, such as antibiotic treatment which is sometimes not successful and accompanied by undesired side effects.

Chronic colonisation with *Pseudomonas aeruginosa* in the respiratory tract of patients with cystic fibrosis (CF) is a principal cause of the high morbidity and mortality in this disease. It is very difficult to get rid of *Pseudomonas aeruginosa* once it has been isolated from the sputum of CF-patients. Only a temporary eradication of this pathogen can be achieved by vigorous antibiotic treatment during very early phases of colonization—and the bacteria will return very soon (1–3). The best results hitherto have been reported from the CF-center in Copenhagen (2) where 14 CF-patients were treated daily with oral ciprofloxacin and inhalation of colistin for 3 weeks at their first *Pseudomonas aeruginosa*-positive culture. After treatment, these CF-patients were observed for up to 27 months (totally 214 months; mean 15.3 months). During this time 2 of the patients became chronically colonized with *Pseudomonas aeruginosa* (defined as six consecutive sputum cultures positive for the bacteria) and there were 49 sputum cultures positive for *Pseudomonas aeruginosa* out of 214 (=23%). From another Copenhagen study it is reported that *Pseudomonas aeruginosa* reoccured in sputum cultures already 4 months after a course of anti-pseudomonas chemotherapy in 98.3% of the CF-patients (3).

Each egg from a hen contains more than 100 mg antibodies. These antibodies are produced by hens and transported to their eggs where they are found in high concentrations. High titres of specific antibodies against bacteria were achieved by repeated immunization of hens with killed specific bacteria or fragments thereof, Specific antibodies against *Pseudomonas aeruginosa* have been produced by repeated immunizations of hens with killed *Pseudomonas aeruginosa*. Eggs from these hens have been used to make a solution with high specific antibody concentration.

An antibody consists of two parts; a Fab fragment which is the part of the antibody that binds to the antigen and a Fc fragment that lack antigen binding properties, The basis of oral administration of immunoglobulins has been attributed to interference with bacterial adherence and neutralization of toxins produced by the pathogens. The protective effect should therefore be conferred by either the whole IgY molecule or the antigen binding fragment thereof since both are capable of above functions. In fact this was demonstrated by the work of Ahren and Svennerholm (5) who observed that Fab fragments of anti-CFA/I reduced fluid secretion (diarrhoea) almost as effectively as non-cleaved immunoglobulin fraction of the serum. Fab fragments from chicken IgY will thus have similar protective functions against bacterial infections as the whole IgY molecule.

In contrast to antibodies from mammals (eg bovine), the antibodies from eggs (6) do not activate the human complement system (7). This is a tremendous advantage since activated complement factors are very effective mediators of inflammatory reactions. In addition, antibodies from eggs do not react with rheumafactors (8), human Fc-receptors (9), bacterial Fc-receptors (10) or human anti-mouse IgG-antibodies (11), which make them very safe to use.

The following examples are provided to further illustrate the invention without being limiting.

EXAMPLE 1

Preparation of avian antibodies against *Pseudomonas aeruginosa*. *Pseudomonas aeruginosa* bacteria were killed by formaldehyde fixation. The killed bacteria were washed in 0.9% NaCl and frozen at −20° C. 0.5 mL of bacteria was mixed with 0.5 mL of Freunds incomplete adjuvant and used for intramuscular immunization of domestic hens. The hens were immunized four times with 2 weeks between the immunizations. The eggs were collected after the initial immunization period of eight weeks and then continuously. The hens recieved further booster immunizations with 2–3 months interval so that they would remain in hyperimmunized condition. The antibodies were purified by the water dilution method according to Akita and Nakai, 1993 (18). After the precipitate had been removed by centrifugation the supernatant was frozen at minus 20° C. in 30–70 mL portions. The antibody titre of the final preparations were checked by immunoblotting.

EXAMPLE II

Case Reports

At their first colonization with *Pseudomonas aeruginosa* in the respiratory tract, two CF-patients were treated with the oral antibiotic ciprofloxacin and antibiotic inhalations of colistin or tobramycin for three weeks. Simultaneously with the antibiotic treatment, they started to gargle daily (for 2 minutes) with the solution according to example 1 and thereafter to swallow specific antibodies against *Pseudomonas aeruginosa*. After this three week period, the patients have continously received antibodies according to the above procedure, but without antibiotics, for together more than 30 months (26 and 4 months, respectively). All sputum cultures during the treatment period have been negative for *Pseudomonas aeruginosa*. (0 positive out of 28=0%; this should be compared with the results from the Copenhagen study, referred to above, which was 49 out of 214=23% p<0.005). Thus, a complete eradication of *Pseudomonas aeruginosa* in the respiratory tract of CF-patients is achieved. The results strongly suggest that the treatment with gargling and swallowing of antibodies against *Pseudomonas aeruginosa* according to the invention is effective to prevent chronic colonization of the bacteria. The effect is with all probability due to the local effect of-the avian antibodies in the oral cavity and/or pharynx, since the antibodies, when swallowed, are degraded by intestinal proteolytic enzymes and are not bloodborne.

For these patients, the dose is preferably about 50 mg IgY per day. Precautions have been made to avoid bacterial contamination of the solutions, which thereafter have been kept at −20° C. The CF-patients have been asked to take out a bottle with 30–70 ml of the solution from the freezer each morning and to gargle with this solution in the evening for 2 minutes and thereafter to swallow it.

Case 1. A 21 year old female with CF. Diagnosed at birth by screening with albumin in meconium (179 mg albumin/g dry weight meconium) and subsequent sweat test (Na 101, Cl 122 mmol/kg sweat). Already during her first three weeks of life there were severe feeding problems. She had frequent stools and was vomiting considerably and her weight went down from 3430 g to 2930 g despite a vigorous appetite. After proper therapy (pancreatic enzymes, breast feeding, extra vitamins, mist tent, physical therapy and anti-staphyloccal antibiotics at every respiratory infection) was instituted she started to gain weight and was doing quite well. Her height was steadily slightly above the mean for her age to a final height of 169 cm; her weight was usually at the mean for her age but had a severe dip at 7–8 years of age and she did not come back to mean weight until 15 years of age. During the last two years her weight has been around 53 kg, ie BMI (body mass index) 18,6. From 7½ years of age she has always had *Staphylococcus aureus* in her sputum and occasionally also *Hemophilus influenzae* or *Proteus mirabilis*. Her chest X-rays showed a slight but steady progress of typical CF-changes and her lung function deteriorated slowly to FVC (forced vital capacity) of about 75%, and FEV1 (forced expiratory volume in one second) to about 50% of predicted values at the age of 19 years. Her first colonization with *Pseudomonas aeruginosa* occurred in November 1989. This was effectively treated with azactam and gentamycin iv in two periods of fourteen days each and addition of ciprofloxain orally at the second course. Thereafter her sputum cultures returned to the earlier pattern of *Staphylococcus aureus* and *Hemophilus influenzae* until August 1994. At this time the bacteria were eliminated after a 14 days course of ceftazidim and tobramycin iv.

However, already in January 1995, *Pseudomonas aeruginosa* was again found in her sputum. At this time it was decided to give her an antibiotic course according to the Copenhagen model (2) with ciprofloxin 750 mg×3 orally and colistin 2 million U×2 by inhalation for three weeks and at the same time start with daily gargling and swallowing of avian antibodies against *Pseudomonas aeruginosa*. The daily intake of antibodies has continued since then (now for 26 months). There has been no new appearence of *Pseudomonas aeruginosa* and the pattern of bacteria in her sputum has returned to the usual. She has never had any precipitins or antibodies against *Psedomonas aeruginosa* in her serum. No side effects of the treatment have been seen in her blood (red and white blood cells, trombocytes, liver enzymes or creatinine values). Her chest X-rays have been essentially unchanged since 1995 as well as her lung function tests (FVC still 75% and FEV1 now 45% of predicted). She is an extremely active woman and her working capacity (150 Watt) must be considered very good in regard to her severe disease.

Case 2. A 17 year old girl with CF During her first two years of life she had recurrent obstructive bronchitis, frequent greasy, foul smelling, loose stools and poor weight gain (weight 9,5 kg at 2 years of age). At this time, sweat tests were performed and revelad the diagnosis of CF. Intensive treatment was then instituted. Her weight came back to mean values but her height followed the −2 SD curve and has stopped at 151 cm. Her main problem has been recurrent stomach ache of the type "distal intestinal obstruction syndrome (DIOS)". Her lungs have always been very good—chest X-rays show only minimal changes, lung function tests have all been at or above mean for her age and height (the exception is RV (residual volume): 1,14=186% of predicted). Her working capacity (120 Watt) is nearly normal. Her sputum cultures had always shown *Staphylococcus aureus* and/or *Hemophilus influenzae* until November 1996 at which time the cultures for the first time showed *Pseudomonas aeruginosa*. She then immediately got a three weeks course of ciprofloxacin 750 mg×2 orally and tobramycin 320 mg×2 by inhalation (colistin was not available). Simultaneously she started daily gargling and swallowing of avian antibodies against *Pseudomonas aeruginosa* with which she has continued since then, Pseudomonas was eradicated and since then (now for 4 months) she has had her usual bacteria in her sputum. She continues to do well.

Equally good results have been achieved for another nine patients and the results strongly suggest a prophylactic and therapeutic effect of the treatment of respiratory tract infection of *Pseudomonas aeruginosa* with avian antibodies against the same according to the invention. In 30 sputum cultures during the therapeutic time period of the two patients described above no *Pseudomonas aeruginosa* positive cultures have been found. In contrast, in the study from Copenhagen referred to above, there were 23% positive cultures, and as many as 75–100% of these patients had at least one positive culture during a similar observation period as in the present invention.

REFERENCES

1. Høiby N., Pseudomonas infection in Cystic fibrosis, In *Cystic Fibrosis*, Current topics, Vol. 1, edited by Dodge J. A., Brock D. J. H. & Widdicombe J. H., John Wiley & Sons Ltd., London, 1993, pp 251–268.
2. Valerius N. H., Koch C., Høiby N., Prevention of chronic *Pseudomonas aeruginosa* colonisation in cystic fibrosis by early treatment; *The Lancel* 1991;338; 725–726
3. Szaff M., Høiby N. and Flensborg E. W.; Frequent antibiotic therapy improves survival of cystic fibrosis patients with chronic *Pseudomonas aeruginosa* infection; *Acta Paediatr Scand* 72:651–657, 1983.
4. Larsson A., Balow R. -M., Lindahl T. L. and Forsberg P. -O. (1993) Chicken IgG: Utilizing the evolutionary advantage; *Poultry Science*, 72, 1807–1812.
5. Ahren C M., Svennerholm A M. (1982) Synergistic protective effect of antibodies against *E. coli* enterotoxin and colonization factor antigens. *Infec. Immun.* 28, 74,
6. Larsson A, and Lindahl T. L. (1993) Chicken antibodies: A tool to avoid interference in immunological assays; *Avian immunology in progress*, 62, 97–102.
7. Larsson A., Wejåker P. -E., Forsberg P. O. and Lindahl T. L. (1992) Chicken antibodies: A tool to avoid interference by complement activation in ELISA; *J. Immunol. Methods* (1992) 156, 79–83.
8. Larsson A. and Sjöquist J. (1988) Chicken antibodies: A tool to avoid false positive results by rheumatoid factor in latex fixation tests; *J. Immunol. Methods* 108, 205–208.
9. Lindahl T. L., Festin R. and Larsson A. (1992), Studies of fibrinogen binding to platelets by flow cytometry: An improved method for detection of platelet activation; *Thrombosis and Haemostasis*, 68, 221–225.
10. Larsson A. and Lindahl T. L. (1993), Chicken antiprotein G for the detection of small amounts of protein G.; *Hybridoma*, 12, 143–147.
11. Larsson A. and Mellstedt H. (1992), Chicken antibodies: a tool to avoid interference by human anti-mouse antibodies in ELISA after in vivo treatment with murine monoclonal antibodies; *Hybridoma* 11, 33–39.
12. Bartz C. R., Conklin R. H., Tunstall C. B. and Steele J. H., Prevention of murine rotavirus infection with chicken egg yolk immunoglobulins; *J. Infect. Dis.*, 142; (1980) 439.
13. Ebina T., Tsukada K., Umezu K., Nose M., Tsuda K., Hatta H., Kim M. and Yamamoto T., Gastroenteritis in suckling mice caused by human rotavirus can be prevented with egg yolk immunoglobulin (IgY) and treated with a protein-bound polysaccharide preparation (PSK); *Microbiol. Immunol.*, 34; (1990) 617.
14. Hiraga C., Kodama Y., Sugiyama T. and Ichikawa Y., Prevention of human rotavirus infection with chicken egg yolk immunoglobulins containing rotavirus antibody in cat; *J. Jpn. Assoc. Infect. Dis.*, 156: (1990) 118.
15. Ikemori Y., Kuroki M., Peralta R. C., Yokoyama H. and Kodama Y., Protection of neonatal calves against fatal enteric colibacillosis by administration of egg yolk powder from hens immunized with K99-piliated enterotoxigenic *Escherichia coli*; *Am. J. Vet. Res.*, 53: (1992) 2005.
16. O'Farrelly C., Branton D. and Wanke C. A., Oral ingestion of egg yolk immunoglobulin from hens immunized with an enterotoxigenic *Escherichia coli* strain prevents diarrhoea in rabbits challenged with the same strain; *Infect, Immun.*, 60: (1992) 2593.
17. European Patent Office publication number 225 254 B1
18. Akita, E M and Nakai, S. (1993) Comparison of four purification methods for the production of immunoglobulins from eggs laid by hens immunized with an enterotoxigenic *E. Coli* strain. *J. Immunol. Methods*, 60, 207–214

What is claimed is:

1. A method for preventing bacterial infection in a patient suffering from cystic fibrosis, who is not currently suffering from a bacterial infection of the lungs and bronchi, comprising:

administering to said patient an amount of avian antibodies against antigens of said bacterial infection sufficient to prevent bacterial infection, wherein said administration is at the oral cavity and pharynx of the patient.

2. The method according to claim 1 wherein the avian antibodies are antibodies against Pseudomonas.

3. The method according to claim 2 wherein said avian antibodies are in a solution and said solution is administered by at least one of gargling and swallowing.

4. The method according to claim 3 wherein said solution is administered by gargling and then optionally swallowing.

5. The method according to claim 1 wherein said avian antibodies are in a solution and said solution is administered by at least one of gargling and swallowing.

6. The method according to claim 5 wherein said solution is administered by gargling and then optionally swallowing.

* * * * *